United States Patent [19]

Fukami et al.

[11] Patent Number: 4,945,104
[45] Date of Patent: Jul. 31, 1990

[54] MALEIMIDE DERIVATIVES AND USE THEREOF IN AGRICULTURAL AND HORTICULTURAL FUNGICIDES

[75] Inventors: Harukazu Fukami, Kyoto; Masaki Hashimoto, Ibaraki; Shinjiro Niwata, Toyonaka; Norio Ohtsuka, Hiratsuka; Fumio Fujita, Yokohama, all of Japan

[73] Assignee: Suntory Limited, Osaka, Japan

[21] Appl. No.: 370,800

[22] Filed: Jun. 23, 1989

[51] Int. Cl.$^5$ .................. A01N 37/32; C07D 207/456
[52] U.S. Cl. .................................. 514/425; 548/547; 548/548
[58] Field of Search ............ 548/547; 71/95; 514/425

[56] References Cited

U.S. PATENT DOCUMENTS 3,894,043 7/1975 Moser et al. .................. 548/548

FOREIGN PATENT DOCUMENTS 2300913 7/1973 Fed. Rep. of Germany .
48-77027 10/1973 Japan .

Primary Examiner—David B. Springer
Attorney, Agent, or Firm—Burns, Doane, Swecker & Mathis

[57] ABSTRACT

A maleimide derivative having the formula (I):

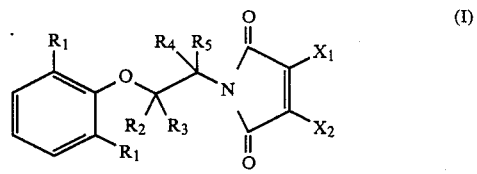

wherein $R_1$ represents a lower alkyl group having 1 to 4 carbon atoms, $R_2$, $R_3$, $R_4$ and $R_5$ independently represent a hydrogen atom, a lower alkyl group having 1 to 4 carbon atoms, a phenyl group which may be substituted, or an aralkyl group having 7 to 10 carbon atoms, and $X_1$ and $X_2$ independently represent a hydrogen atom or a halogen atom, and a production process thereof as well as a agricultural and horticultural fungicide containing, as an active ingredient, the maleimide derivative.

3 Claims, No Drawings

MALEIMIDE DERIVATIVES AND USE THEREOF IN AGRICULTURAL AND HORTICULTURAL FUNGICIDES

BACKGROUND OF THE INVENTION

1. Field of the Invention

The present invention relates to a maleimide derivative having the general formula (I):

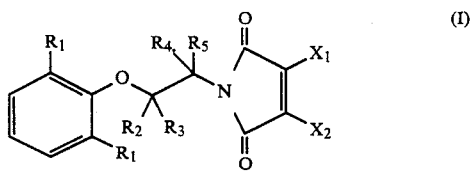

wherein $R_1$ represents a lower alkyl group having 1 to 4 carbon atoms, $R_2$, $R_3$, $R_4$, and $R_5$ indepentently represent a hydrogen atom, a lower alkyl group having 1 to 4 carbon atoms, a phenyl group which may be substituted, or an aralkyl group having 7 to 10 carbon atoms, and $X_1$ and $X_2$ independently represent a hydrogen atom or a halogen atom, a process for the preparation of this maleimide derivative, and an agricultural and horticultural fungicide containing this maleimide derivative as an active ingredient.

Typical examples of the lower alkyl group $R_1$ in the general formula (I) are a methyl group, an ethyl group, and an n-propyl group, and typical examples of the lower alkyl group $R_2$, $R_3$, $R_4$ or $R_5$ are a methyl group, an ethyl group, an n-propyl group, and an isopropyl group. Typical phenyl groups which may be substituted are a phenyl group, a chlorophenyl group, and a tolyl group, and a benzyl group is a typical instance of the aralkyl group. Typical examples of the halogen atom $X_1$ or $X_2$ are a chlorine atom and a bromine atom.

2. Description of the Related Art

In connection with maleimide derivatives, Japanese Unexamined Patent Publication (Kokai) No. 48-77027 teaches that a compound having the following general formula:

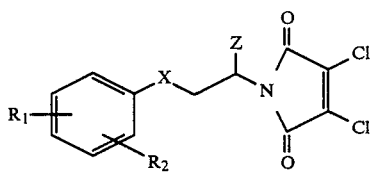

wherein Z represents a hydrogen atom or a methyl group, X represents an oxygen atom, a sulfur atom, a group NH or an N-methyl group, $R_1$ represents a hydrogen atom, a chlorine atom, a bromine atom or a trifluoromethyl group, and $R_2$ represents a hydrogen atom, a halogen atom, a methyl group, or a trifluoromethyl group, is effective as an agent for controlling harmful organisms. Although this compound resembles the compound of the present invention represented by the general formula (I), the 2,6 dimethylphenoxy derivative is not specifically mentioned in the above-mentioned patent publication.

It is taught that the compound disclosed in Japanese Unexamined Patent Publication (Kokai) No. 48-77027 is effective for controlling *Botrytis cinera*, *Phakaosora pachrhizi*, *Podosphaera leucotricha*, *Uncinule necator*, *Cercosoora zonata*, *Puccinia recondita*, and *Pyricularia oryzae*.

SUMMARY OF THE INVENTION

Accordingly, the objects of the present invention are to eliminate the above-mentioned disadvantages of the prior art and to provide a novel maleimide derivative, which is more effective for controlling *Pyricularia oryzae*, *Phizoctonia solani*, and *Phytophthora infestans*.

Other objects and advantages of the present invention will be apparent from the following description.

In accordance with the present invention, there is provided a maleimide derivative having the formula (I):

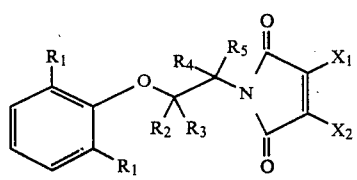

wherein $R_1$ represents a lower alkyl group having 1 to 4 carbon atoms, $R_2$, $R_3$, $R_4$ and $R_5$ independently represent a hydrogen atom, a lower alkyl group having 1 to 4 carbon atoms, a phenyl group which may be substituted, or an arylkyl group having 7 to 10 carbon atoms, and $X_1$ and $X_2$ independently represent a hydrogen atom or a halogen atom.

DESCRIPTION OF THE PREFERRED EMBODIMENTS

The maleimide derivative having the above-mentioned general formula (I) can be prepared according to the following process A or B:

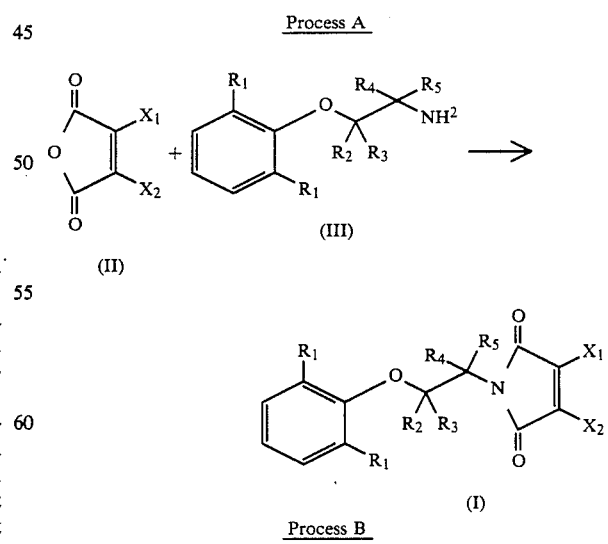

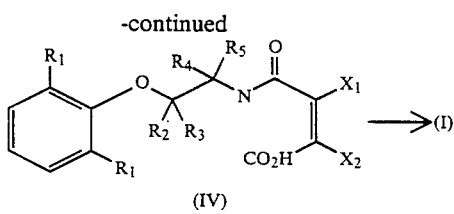

In the above reaction formulae, $R_1$, $R_2$, $R_3$, $R_4$, $R_5$, $X_1$ and $X_2$ are as defined in the general formula (I).

According to the process A, a corresponding acid anhydride (II) is reacted with an amine derivative under reflux in an organic acid such as acetic acid or in a non-protonic solvent such as toluene or xylene. According to the process B, the acid anhydride (II) is reacted with the amine derivative (III) at a temperature of from room temperature to the boiling point in a non-protonic solvent, for example, an ether type solvent such as ether, tetrahydrofuran or dioxane, a benzene type solvent such as benzene or toluene, an ester type solvent such as ethyl acetate, or acetone, to form a maleic acid amide derivative (IV), and the derivative (IV) is then reacted at a temperature of from 80° to 200° C. in the absence of a solvent or in the presence of a solvent such as toluene, xylene or a paraffinic solvent. In each process, the reaction time greatly differs according to the kind of solvent used, but the reaction time is generally from 10 minutes to 12 hours.

The compound of the general formula (I) obtained according to the above-mentioned process in the present invention exerts curative and protective effects as an agricultural and horticultural fungicide against diseases of plants, by application to the soil or scattering same on stems and leaves. The compound of the general formula (I) is especially effective against such diseases as blast and sheath blight of rice and late blight of tomato.

The compound of the present invention is mixed with a carrier and, optionally, with other adjuvants, and the mixture is formed into a preparation customarily adopted for an agricultural and horticultural fungicide, such as dust, coarse dust, fine dust, granules, a wettable powder, an emulsifiable liquor, a suspension or an aqueous solution. As appropriate examples of the liquid carrier, there can be mentioned water, alcohols such as ethanol and ethylene glycol, ketones such as acetone, ethers such as dioxane and cellosolve, aliphatic hydrocarbons such as kerosene and kerosine, aromatic hydrocarbons such as benzene and toluene, organic bases such as pyridine, halogenated hydrocarbons such as chloroform and tetrachloromethane, esters such as ethyl acetate and fatty acid glycerol esters, nitriles such as acetonitrile, and dimethyl formamide and dimethyl sulfoxide.

As appropriate examples of the solid carrier, there can be mentioned plant powders (such as starch and wheat flour) and mineral powders (such as kaolin, betonite, calcium phosphate, clay, talc, and silica). These carriers can be used singly or in the form of a mixture of two or more thereof.

Surface active agents such as soaps, higher alcohol sulfate esters, alkyl-sulfonic acids, alkylaryl-sulfonic acids, quaternary ammonium salts, hydroxyalkylamines, fatty acid esters, polyalkylene oxide type surfactants, and anhydrosorbitol type surfactants can be optionally used as an emulsifier, a spreading agent, a penetrant, a dispersant or the like. Preferably, the surfactant is contained in an amount of 0.2 to 10% by weight in the chemical preparation. Other fungicides, an insecticide, a nematocide, a herbicide, a plant growth modifier, a plant nutrient, a fertilizer, a soil modifier, and the like can be appropriately added according to need.

The agricultural and horticultural fungicide of the present invention can be prepared from the maleimide derivative (I), the carrier, and auxiliary components by a known process or a process analogous thereto.

In the agricultural chemical preparation of the present invention, preferably the content (% by weight) of the active compound (I) is about 5 to 90% in the case of an emulsifiable liquor or wettable powder, about 0.1 to about 20% in the case of oil or dust, and about 1 to about 50% in the case of granules. Furthermore, preferably an emulsifiable liquor or wettable powder is appropriately diluted (for example, 50 to 5000 times) with water or the like at the time of application, and the dilution is scattered.

The amount used of the compound (I) of the present invention, the combination with other chemicals, and the mixing ratio are changed according to the growth stage of the objective plant, the growth condition, the kind of pathogenic bacterium, the disease state, the chemical application time, and the application method. In general, however, the application rate is adjusted so that the amount scattered of the compound (I) is 10 to 300 g per 10 ares. The applied concentration of the compound (I) is adjusted to 10 to 1000 ppm. As the application method, there can be mentioned scattering, dusting, irrigation, and seed coating. In the present invention, the amount used of the chemical, the applied concentration, and the application method are not particularly critical, as long as the fungicide can be safely and effectively applied to the plants.

EXAMPLES

The present invention will now be described in detail with reference to the following Examples, Preparation Examples, and Experiments, that by no means limit the technical scope of the present invention. Note, the procedures of the fungicidal experiment will be described hereinafter.

EXAMPLE 1 (Process A)

Production of N-[(2,6-dimethylphenoxy)ethyl]-3,4-dichloromaleimide (Compound No. 2)

In 20 ml of glacial acetic acid were dissolved 1.4 g of (2,6-dimethylphenoxy)ethylamine and 1.0 g of 3,4-dichloromaleic anhydride, and the silution was refluxed for 4 hours. After termination of the reaction, the reaction liquid was concentrated under a reduced pressure, and the obtained residue was purified by silica gel chromatography [eluted with hexane/ethyl acetate (9/1)] to obtain 1.2 g of the intended compound in the form of a white crystal.

EXAMPLE 2 (PROCESS B)

Production of [{2-methyl-2-(2,6-dimethylphenoxy)}ethyl]-3-bromomaleimide (Compound No. 6)

In 10 ml of tetrahydrofuran were dissolved 0.7 g of [2-methyl-2-(2,6-dimethylphenoxy)]ethylamine and 0.76 g of 3-bromomaleic anhydride, and the solution was heated and refluxed for 1 hour. The reaction liquid was concentrated under a reduced pressure and the obtained residue was dissolved in 5 ml of anhydrous acetic acid, 20 mg of sodium acetate was added to the solution, and the reaction was carried out at 100° C. for 3 hours. The reaction liquid was concentrated under a reduced pressure and the residue was dissolved in ethyl acetate, washed with water, and dried with magnesium sulfate. The solvent was then removed by distillation.

The obtained residue was purified by silica gel chromatography [eluted with n-hexane/ethyl acetate (9/1)] to obtain 0.72 g of the intended compound.

EXAMPLE 3 (PROCESS B)

Production of N-[(2-isopropyl-2-(2,6-dimethylphenoxy)ethyl]-3,4-dichloromaleimide Compound No. 3

In 15 ml of tetrahydrofuran were dissolved 1.62 g of [2-isopropyl-2-(2,6-dimethylphenoxy)ethylamine and 1.57 g of 3,4-dichloromaleic anhydride, and the solution was heated and refluxed for 1 hour. The solvent was removed by distillation, the residue was suspended in 20 ml of toluene, and the suspension was heated and refluxed for 8 hours. The reaction liquid was concentrated under a reduced pressure, and the residue was purified by silica gel chromatography [eluted with n-hexane/ethyl acetate (8/1)] to obtain 1.3 g of the intended compound.

Compound Nos. 1, 4, 5 and 7 through 14 were synthesized according to any of the processes disclosed in Examples 1 through 14. These compounds and their physical properties are shown in Table 1.

PREPARATION EXAMPLE 3 (EMULSIFIABLE LIQUOR)

Nine parts of compound No. 2, 10 parts of ethylene glycol, 20 parts of dimethyl formamide, 10 parts of alkyldimethyl ammonium chloride, and 52 parts of methanol were mixed and dissolved to obtain 100 parts of an emulsifiable liquor.

PREPARATION EXAMPLE 4 (GRANULE)

Ten parts of compound No. 2, 15 parts of starch, 72 parts of bentonite, and 3 parts of a sodium salt of lauryl sulfate were mixed and pulverized to obtain 100 parts of a granule.

EXPERIMENT 1 (EFFECT OF CONTROLLING FUNGUS CAUSING RICE BLAST)

(Experimental procedures)

Thirty budding seeds of a paddy-rice plant (variety: Nipponbare) were directly sown in a pot and the growth was conducted to the 2-leaf or 3-leaf stage in a greenhouse. The wettable powder prepared according to the process of Preparation Example 1 was diluted to a predetermined concentration with water and the dilution was scattered on the rice seedlings at an application rate of 30 ml per 3 pots by a spray gun. After standing for one day in a greenhouse, the seedlings were inoculated with the blast-causing fungus (*Pyricularia oryzae*).

TABLE 1

Maleimide Derivatives of General Formula (I)

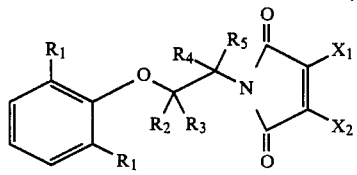

| Compound | $R_1$ | $R_2$ | $R_3$ | $R_4$ | $R_5$ | $X_1$ | $X_2$ | Physical Properties |
|---|---|---|---|---|---|---|---|---|
| 1 | Me | Me | H | H | H | Cl | Cl | m.p. 106.0° C. |
| 2 | Me | H | H | H | H | Cl | Cl | m.p. 116.0° C. |
| 3 | Me | i-Pro | H | H | H | Cl | Cl | m.p. 138.0° C. |
| 4 | Me | Me | Me | H | H | Cl | Cl | m.p. 112.0° C. |
| 5 | Me | Me | H | H | H | Br | Br | m.p. 119.0° C. |
| 6 | Me | Me | H | H | H | Br | H | m.p. 88.5° C. |
| 7 | Me | Et | H | H | H | Cl | Cl | m.p. 107.5° C. |
| 8 | Me | n-Pro | H | H | H | Cl | Cl | m.p. 74.5° C. |
| 9 | Me | H | H | Me | H | Cl | Cl | $n_D^{35}$ 1.5462 |
| 10 | Me | Ph | H | H | H | Cl | Cl | m.p. 105.0° C. |
| 11 | Me | 4-ClPh | H | H | H | Cl | Cl | m.p. 102.0° C. |
| 12 | Me | H | H | Ph | H | Cl | Cl | m.p. 108.5° C. |
| 13 | Me | H | H | CH$_2$Ph | H | Cl | Cl | m.p. 108.0° C. |
| 14 | Me | H | H | H | H | Br | Br | m.p. 135.0° C. |
| Comparative compound | H | H | H | H | H | Cl | Cl | m.p. 70.5° C. |

PREPARATION EXAMPLE 1 (WETTABLE POWDER)

A mixture of 10 parts by weight (all of "parts" given hereinafter are by weight) of compound No. 2, 5 parts of sodium lauryl sulfate, 2 parts of a sodium dinaphthylmethanedisulfonate/formalin condensate, and 83 parts of clay was pulverized to obtain 100 parts of a wettable powder.

PREPARATION EXAMPLE 2 (DUST)

A mixture of 0.2 part of compound No. 2, 0.5 part of calcium stearate, 50 parts of talc, and 49.3 parts of clay was pulverized to obtain 100 parts of a dust.

The inculation source was a suspension of spores (spore concentration = $5 \times 10^5$ spores per ml) of *Pyricularia oryzae* formed and grown in a rice straw extract-agar medium, and the spore suspension was applied by a spray gun.

After the inoculation, the seedlings were allowed to stand in a greenhouse at 26° C. for 24 hours, and the seedlings were grown in the greenhouse at 25° C. for 7 days while sheltered from the direct rays of the sun, to allow an outbreak of the disease. The number of disease spots per pot was counted and the control value was calculated according to the following equation:

$$\text{Control value} = \left(1 - \frac{\begin{array}{c}\text{total number of disease}\\\text{spots in treated}\\\text{section}\end{array}}{\begin{array}{c}\text{total number of disease}\\\text{spots in untreated}\\\text{section}\end{array}}\right) \times 100$$

Experimental Results

The control effects of the tested compounds are shown in Table 2.

TABLE 2

| Compound No. | Scattered Concentration (ppm) | Control Value |
| --- | --- | --- |
| 1 | 500 | 100.0 |
| 2 | 500 | 100.0 |
| 3 | 500 | 80.0 |
| 4 | 500 | 98.0 |
| 5 | 500 | 94.1 |
| 6 | 500 | 100.0 |
| 7 | 500 | 100.0 |
| 8 | 500 | 100.0 |
| 9 | 500 | 95.7 |
| 10 | 500 | 95.8 |
| 13 | 500 | 92.9 |
| Comparative compound | 500 | 59.4 |

EXPERIMENT 2 (EFFECT OF CONTROLLING FUNGUS CAUSING SHEATH BLIGHT IN RICE)

(Experimental Procedures)

The wettable powder prepared according to the process described in Preparation Example 1 was diluted to a predetermined concentration and the dilution was applied at a rate of 30 ml per pot, by a spray gun, to rice plants (variety: Nipponbare) (three rows per section) during or after the earing stage. One day after the chemical treatment, the rice plants were inoculated with the sheath blight-causing fungus (Phizoctonia solani). The bacterium was cultured in PAS medium (in Petri dish having a diameter of 9 cm) at 28° C. for 2 days, the obtained cells and the culture medium were enclosed with gauze, and the enclosure was used as the inoculation source and placed on the roots of the culms cells of ¼ Petri dish per pot to effect inoculation. Then, the inoculated rice plants were placed in a moisture chamber maintained at 30° C. and allowed to stand in a greenhouse maintained at 30° C. for 7 days, the maximum disease spot in each culm was measured, and the control value was calculated according to the following equation:

$$\text{Control value} = \left(1 - \frac{\begin{array}{c}\text{average maximum}\\\text{disease spot length}\\\text{per culm in treated}\\\text{section}\end{array}}{\begin{array}{c}\text{average maximum}\\\text{disease spot length}\\\text{per culm in untreated}\\\text{section}\end{array}}\right) \times 100$$

Experimental Results

The control effects of the tested compounds are shown in Table 3.

TABLE 3

| Compound No. | Scattered Concentration (ppm) | Control Value |
| --- | --- | --- |
| 2 | 500 | 100.0 |
| 4 | 500 | 100.0 |
| 5 | 500 | 100.0 |
| 10 | 500 | 100.0 |
| Comparative compound | 500 | 0.0 |

EXPERIMENT 3 (EFFECT OF CONTROLLING FUNGUS CAUSING LATE BLIGHT OF TOMATO)

The wettable powder prepared according to the process described in Preparation Example 1 was diluted to a predetermined concentration with water and the dilution was scattered at a rate of 30 ml per 3 pots on tomato seedlings (variety: Red Cherry) grown to the 5-leaf or 6-leaf stage after sowing. One day after the chemical treatment, the seedlings were inoculated with the late blight-causing fungus (Phytophthora infestans). The zoosporangia formed on the tomato leaves were scratched off, the concentration of the zoosporangia was adjusted to $5 \times 10^5$ zoosporangia per ml, and the zoosporangia were maintained at 13° C. for about 1 hour. After confirmation of an indirect germination of zoospores (at least 40%), the tomato seedlings were inoculated with the zoosporangia by a spray gun. Then the tomato seedlings were placed in a moisture chamber maintained at 20° C. and allowed to stand in a greenhouse maintained at 25° C. for 2 days. With respect to 3 to 4 leaves per stalk, the disease spot area was examined in 10 ranks, and the control value was calculated according to the following equation:

$$\text{Control value} = \left(1 - \frac{\begin{array}{c}\text{disease index in}\\\text{treated section}\end{array}}{\begin{array}{c}\text{disease index in}\\\text{untreated section}\end{array}}\right) \times 100$$

(Experimental Results)

The control effects of the tested compounds are shown in Table 4.

TABLE 4

| Compound No. | Scattered Concentration (ppm) | Control Value |
| --- | --- | --- |
| 1 | 500 | 88.9 |
| 2 | 500 | 100.0 |
| 5 | 500 | 78.4 |
| 6 | 500 | 96.7 |
| 8 | 500 | 94.2 |
| 9 | 500 | 89.7 |
| 12 | 500 | 77.8 |
| Comparative compound | 500 | 54.4 |

We claim:

1. A maleimide derivative having the formula (I):

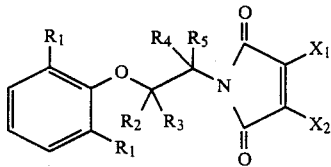

wherein $R_1$ represents a lower alkyl group having 1 to 4 carbon atoms, $R_2$, $R_3$, $R_4$ and $R_5$ independently represent a hydrogen atom, a lower alkyl group having 1 to 4 carbon atoms, a phenyl group, a chlorophenol group, a tolyl group or an aralkyl group having 7 to 10 carbon atoms, and $X_1$ and $X_2$ independently represent a hydrogen atom or a halogen atom.

2. A compound as claimed in claim 1, wherein $R_1$ is a methyl group.

3. An agricultural and horizontal fungicide comprising, as an active ingredient, a maleimide derivative represented by the formula (I) of claim 1.

* * * * *